(12) United States Patent
Rothen-Weinhold et al.

(10) Patent No.: US 6,319,512 B1
(45) Date of Patent: Nov. 20, 2001

(54) IMPLANTS FOR CONTROLLED RELEASE OF PHARMACEUTICALLY ACTIVE PRINCIPLES AND METHOD FOR MAKING SAME

(75) Inventors: Alexandra Rothen-Weinhold, Croix-de-Rozon; Robert Gurny, Geneve; Piero Orsolini, Martigny; Frédéric Heimgartner, Villeneuve, all of (CH)

(73) Assignee: Debio Recherche Pharmaceutique SA (CH)

( * ) Notice: Subject to any disclaimer, the term of this patent is extended or adjusted under 35 U.S.C. 154(b) by 0 days.

(21) Appl. No.: 09/424,936

(22) PCT Filed: Jun. 2, 1998

(86) PCT No.: PCT/EP98/03270
§ 371 Date: Feb. 23, 2000
§ 102(e) Date: Feb. 23, 2000

(87) PCT Pub. No.: WO98/55101
PCT Pub. Date: Dec. 10, 1998

(30) Foreign Application Priority Data

Jun. 4, 1997 (FR) .................................................. 97 06874

(51) Int. Cl.$^7$ .............................. A61K 9/00; A61K 38/00
(52) U.S. Cl. .......................... 424/425; 424/422; 424/423; 424/424; 424/464; 424/465; 424/468; 424/474; 424/475; 424/482; 424/484; 424/486; 514/2; 514/9; 514/11; 514/806
(58) Field of Search ................................. 424/422, 423, 424/424, 427, 428, 430, 434, 435, 425, 464, 465, 468, 474, 475, 482, 484, 486; 514/2, 9, 11, 806

(56) References Cited

U.S. PATENT DOCUMENTS

| | | | |
|---|---|---|---|
| 4,828,561 | * 5/1989 | Woodroof | 623/8 |
| 4,894,231 | 1/1990 | Moreau | 424/426 |
| 5,011,692 | * 4/1991 | Fujioka et al. | 424/426 |
| 5,192,741 | * 3/1993 | Orsolini et al. | 514/4 |
| 5,496,557 | * 3/1996 | Feijen et al. | 424/426 |
| 5,851,547 | * 12/1998 | Fujioka et al. | 424/426 |
| 5,985,305 | * 11/1999 | Peery et al. | 424/422 |

FOREIGN PATENT DOCUMENTS

| | | |
|---|---|---|
| 0 659 406 | 6/1995 | (EP) . |
| WO 91/11176 | 8/1991 | (WO) . |
| WO 92/14450 | 9/1992 | (WO) . |
| WO 94/03159-A1 | * 2/1994 | (WO) . |
| WO 96/12466-A1 | * 5/1996 | (WO) . |

OTHER PUBLICATIONS

Rothen–Weinhold—<<Development of a long term delivery system for RC–160, a somastostin analog>> XP–002055081 (1997).

* cited by examiner

Primary Examiner—Jose' G. Dees
Assistant Examiner—Frank Choi
(74) Attorney, Agent, or Firm—Piper Marbury Rudnick & Wolfe

(57) ABSTRACT

The present intention relates to an implant for the controlled release of at least one pharmaceutically active principle comprising a core containing at least one active principle and a sheath surrounding said core, wherein said sheath is composed of at least one polymeric film applied around said core. It also relates to a process for the preparation of such an implant, characterised by the production of a core containing at least one active principle, preparation of at least one polymeric film, application of the polymeric film(s) around said core by juxtaposition and/or superposition thereof, and sterilisation of the implant thus obtained.

11 Claims, 1 Drawing Sheet

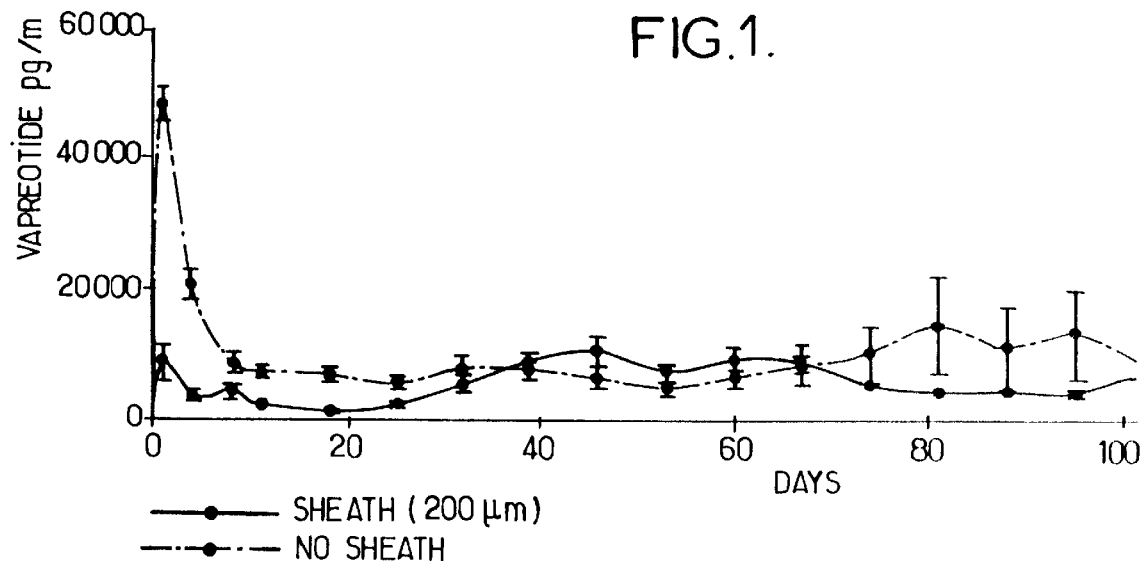
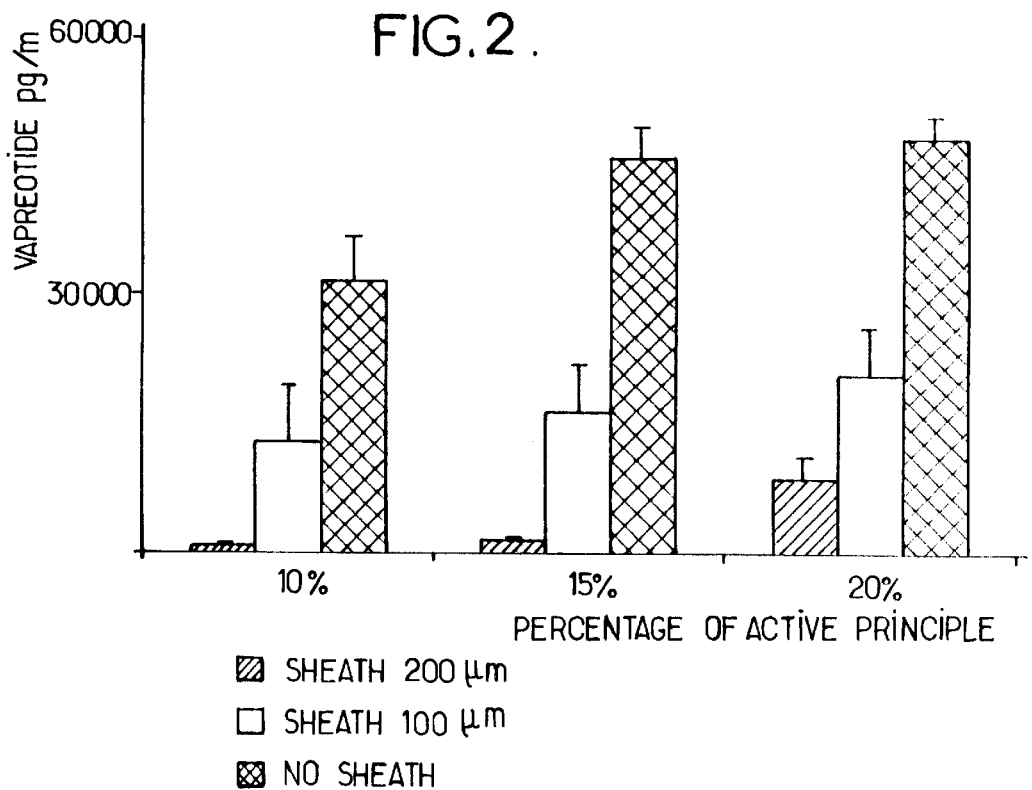

IMPLANTS FOR CONTROLLED RELEASE OF PHARMACEUTICALLY ACTIVE PRINCIPLES AND METHOD FOR MAKING SAME

The present invention relates to an implant for the controlled release of pharmaceutically active principles. It also relates to a process for the production of such an implant.

Controlled release formulations of medicinal products are extremely useful for the administration of medical and pharmaceutical products and have a wide variety of applications in which they offer numerous advantages in comparison with standard formulations of medicinal products.

A single administration of a controlled release formulation ensures the slow release of the active principle over a prolonged period.

One of the prime applications of this type of controlled release formulation lies in the field of drug addiction. The treatment of patients who are addicted to the use of drugs is rendered awkward and difficult in so far as, with standard formulations, it is not always easy to obtain the patient's cooperation. Thus, with standard formulations, there is always the risk that the patient will refuse to follow the necessary treatment at the desired time. With controlled release formulations, a single administration, on the other hand, ensures an effective treatment for a certain period, superior to that which can be obtained from a single dose.

Controlled release formulations of medicinal products are also particularly useful in applications such as anti-cancer therapy where long term treatments are often required.

Another important application for these formulations lies in the field of hormone therapy, for example, relating to contraceptives where the continuous release of the active principle in a relatively constant concentration is required over a certain period.

Controlled release formulations of medicinal products may be proposed in a variety of pharmaceutical forms. Thus, there exist formulations of implants and formulations permitting oral or parenteral administration.

Oral formulations are normally in the form of tablets or capsules which may easily be swallowed or ingested.

Parenteral formulations often have a spherical structure. They suffer from the constraint of size because they have to be able to be introduced into the patient's body by injection using a needle of a reasonable diameter. Said formulations are often produced using granulation or microencapsulation processes.

Implants may take several forms. They are thus often moulded in the form of films then treated to give different shapes, such as cylindrical rods, spherical particles and others.

Depending on the purpose and the circumstances of the desired form of therapy, implants may sometimes be preferred to carenteral formulations. This preference exists particularly if a certain flexibility is desired with respect to the treatment protocol. Compared with parenteral formulations, implants have the advantage of being able to be removed surgically if it should prove necessary to stop the treatment before the complete release of the active principle has taken place.

A phenomenon often observed with controlled release formulations of medicinal products is that of the "burst effect", that is, a very large initial release of the active principle. In certain cases, this effect may be desirable. On the other hand, there are cases where it may prove to be dangerous. This is the case particularly as regards hormone therapies which use active principles having very troublesome or even toxic side-effects in high concentrations. In such cases, it is imperative to be able to ensure slow and uniform release in small quantities of the active principle.

The patent application EP 0 659 406 in the names of DOW CORNING ASIA Ltd. and SUMITOMO PHARMACEUTICALS COMPANY Ltd. provides a possible solution to the problem described above. This application describes a cylindrical rod of controlled release formulation comprising an internal layer which does not disintegrate and an external layer which is impermeable to water. In the examples of this application, one may read that this formulation is prepared by immersing the internal layer in a solution containing the substance which constitutes the external layer or coating. This method known as "dipping" or immersion is also described in the U.S. Pat. No. 4,894,231 in the name of BIOMEASURE, Inc. In this patent, the external layer is also a substance which is impermeable to water which acts as a "barrier", thus also preventing an excessively large initial release of the active principle.

This patent, apart from the dipping method, also describes the coating of the internal layer with an external layer by spraying.

All the implants or other controlled release formulations of medicinal products produced by the methods described above suffer, however, from several shortcomings.

The formation of the external layer by methods such as dipping or spraying makes it very difficult or cumbersome to obtain a layer with a smooth and uniform surface. These methods also have the disadvantage of not permitting reliable control of the thickness of the layer. It would be very desirable, however, to be able to obtain, by a simple method, implants comprising a smooth and uniform external layer, with a chosen thickness, which would also make it possible to control more effectively or even limit the "burst effect".

The methods known as dipping have an additional disadvantage. In fact, these methods require the use of organic solvents such as acetone, chloroform or methylene chloride. It is necessary, therefore, to remove said solvents in order to be able to introduce the implants or other formulations into the body of the patient to be treated.

The applicant company, after considerable work and research, has managed to respond to the existing need for an implant for he controlled release of pharmaceutically active principles for which the "burst effect" is appreciably controlled whilst avoiding the disadvantages of the formulations described in the prior art.

The invention provides, therefore, an implant for the controlled release of at least one pharmaceutically active principle, said implant comprising a core which contains at least one active principle and a sheath which surrounds said core, and is wherein said sheath is composed of at least one polymeric film applied around said core.

According to a preferred embodiment of the invention, the sheath is composed of at least two polymeric films, one surrounding part of the core and the other surrounding the remaining part.

The sheath consists of at least one polymeric film applied around the core. Thus, it is possible to have a sheath consisting of:

at least two identical or different polymeric films which are each applied around a part of the core as indicated above, or at least two identical or different superposed polymeric films applied around the core.

Of course, the sheath may also consist of the two polymeric films juxtaposed in order to surround the whole of the core onto which is applied at least one other polymeric film.

The implant according to the invention has the advantage of having a perfectly smooth and uniform sheath, the thickness of which may be chosen, which permits great flexibility in terms of the choice of the release profile, thus offering the possibility of a more precise regulation of the "burst effect" and thus of the initial rate of release of the pharmaceutically active principle. This thickness may be controlled as a function of the thickness of the polymeric film chosen and the number of superposed polymeric films applied around the core.

Advantageously, the core is composed of a biodegradable polymer mixed with at least one pharmaceutically active principle.

The sheath may also be composed of a biodegradable polymer, this possibly being the same polymer as that forming the core, or another polymer.

The polymer of the sheath may optionally be mixed beforehand with one or more pharmaceutically active principles. Said active principles may optionally be the same as those which are combined with the polymer forming the core.

The biodegradable polymers used in the implant according to the invention may be chosen from the group comprising: polycaprolactones, polyorthoesters, polyanhydrides, polyacetals and α-hydroxycarboxylic acids such as the homopolymers and copolymers of lactic acid, glycolic acid and succinic acid.

In fact, the discovery of readily biodegradable polymers has advanced the technology considerably in the field of delayed release drug formulations. It is, of course, advantageous to be able to introduce a polymer drug formulation into the human or animal body knowing that the polymer is going to degrade over a certain period of time, allowing a slow release of the medicinal product without leaving behind any foreign bodies in the patient's body.

As regards biodegradable polymers, the copolymers and homopolymers of lactic and glycolic acids are particularly preferred in the controlled release implants according to the invention. They are readily degradable, decompose to harmless products such as carbon dioxide and water and do not, therefore, leave any residue over time after the release of the active principle.

Said polymers will generally be called "polylactides" here.

In the context of the present invention, the term "polylactides" aims to include both its generic meaning, that is, a polyester derived from an α-hydroxycarboxylic acid, and its specific meaning, that is, a polymer derived from lactic acid (α-hydroxypropionic acid). The term is also assumed to include copolymers of glycolic and lactic acids as well as homopolymers of either of said acids.

The polylactides advantageously used to form the core of the implant are low molecular weight L-polylactic acids. Said polymers have a molecular weight in the range 2000 daltons to 30000 daltons, preferably in the range 2000 daltons to 15000 daltons and even more preferably in the range 4000 daltons to 6000 daltons, most preferably 5000 daltons.

The sheath of the implant according to the invention is advantageously composed of a mixture of a polylactide-co-glycolide) acid polymer (PLGA) and a polylactide acid polymer (PLA). Preferably, the mixture is prepared in proportions in the range 40:60 to 60:40 and more preferably 50:50. The molecular weight of the PLGA used is advantageously in the range 20000 daltons to 100000 daltons, preferably in the range 40000 daltons to 60000 daltons and even more preferably 55000 daltons. The molecular weight of the polylactide acid used is preferably in the range 2000 daltons to 6000 daltons and even more preferably 5000 daltons.

Of course, the sheath may be composed of just one of said polymers or of any other combination of the polymers mentioned above.

However, after considerable research, the applicant company ascertained that the polymer consisting of a specific mixture in proportions of 50/50 by weight of a poly(lactide-co-glycolide) acid having a molecular weight of 55000 daltons and a polylactide acid having a molecular weight of 5000 daltons makes it possible to obtain a sheath which is particularly suitable for the controlled release of a pharmaceutically active principle.

In fact, the poly(lactide-co-glycolide) acid polymer mentioned above has, by itself, a certain number of advantages such as obtaining homogeneous films having a quasi-immediate onset of degradation. However, it suffers from the disadvantage that the films obtained are very brittle and thus not suitable for use as a sheath.

As regards the polylactide acid polymer, it gives films which are not brittle. On the other hand, said films are not homogeneous and their rate of degradation is not very fast.

The applicant company has ascertained, contrary to all expectations, that the combination of these two polymers would make it possible to obtain homogeneous, non-brittle films having a rate of degradation perfectly suitable for forming the sheath of the implant for the release of the pharmaceutically active principle.

Thus, the invention also relates to a polymer intended to form the sheath of an implant for the controlled release of at least one pharmaceutically active principle.

Said polymer is composed of a mixture of:
  a poly(lactide-co-glycolide) acid having a molecular weight in the range 20000 daltons to 100000 daltons, preferably in the range 40000 daltons to 60000 daltons, and even more preferably 55000 daltons, and
  a polylactide acid having a molecular weight in the range 2000 daltons to 6000 daltons, preferably 5000 daltons.

Advantageously, the weight ratio of the two constituents of the mixture is in the range 40:60 to 60:40, and is preferably 50:50.

The implants according to the present invention make it possible, thanks to the judicious choice of the polymers forming the core and the sheath, to adjust the release time and the release profile of an active principle.

Thus, depending on the hydrophilic/hydrophobic interactions between the polymers and the active principle(s), it is possible to obtain a faster or slower release.

Moreover, it is possible to modify the release profile. For example, by choosing for the sheath a polymer which degrades very rapidly, it is possible to obtain a large immediate release. However, if a polymer that is not readily degradable is chosen for the sheath, this initial release is diminished.

Surprisingly and unexpectedly, the applicant company has observed that the implants according to the invention permit a regular release of the active principle, even after the sheath has disappeared. In fact, one might have expected there to be a "burst effect" after dissolution of the sheath, but this does not happen.

BRIEF DESCRIPTION OF THE DRAWINGS

FIG. 1 shows that the initial "burst effect" is almost entirely eliminated for the implants according to the invention in comparison with implants composed solely of a core and, moreover, that there is no delayed "burst effect".

FIG. 2 shows the effect of the thickness of the sheath on the "burst effect". The initial release of active principle is very large for an implant not comprising a sheath compared with implants according to the invention having sheaths with a thickness of 100 µm or 200 µm.

According to the present invention, it is also possible to establish release protocols for more than one active principle. Thus, if the polymer forming the core contains an active principle and the polymer of the sheath also contains an active principle which is the same or different, it is possible to obtain complex release protocols in which the active principle(s) may be released simultaneously or consecutively.

Thus, the structure of the implants according to the invention offers a greater flexibility in the choice of release rates and profiles for the various types of active principles.

The wide variety of active principles which may be used within the context of the invention include hormones, enzymes, polypeptides, proteins, vaccines, antibiotics, anti-cancer substances and other bioactive substances.

According to one particular embodiment of the invention, the active principle is an analogue of somatostatin or one of the pharmaceutically acceptable salts thereof. Preferably, said active principle is vapreotide pamoate.

The invention also provides a process for the production of the implants for the controlled release of at least one active principle.

Said process is wherein:

a core containing at least one active principle is produced, at least one polymeric film is prepared, said polymeric film(s) is/are applied around said core, thus forming a sheath, the implant thus obtained is sterilised.

Production of the core may be carried out by any method known to the skilled person, such as extrusion or by moulding. Preferably, a mixture of the polymer with the active principle is prepared, the mixture is homogenised and extrusion is carried out at a temperature chosen as a function of the nature of the polymer and of the active principle.

The polymeric film is prepared by any known method. Preferably, the chosen polymer(s) is/are heated and the mixture is subjected to hydraulic pressure at a temperature chosen in terms of the nature of the polymers.

The polymeric film may undergo an intermediate moulding step by which the thickness of the film is better controlled. To do this, the film is placed in a concave "female" part of a mould, the convex "male" part is placed on top such that there is a space of the desired thickness between the two parts of the mould. Pressure is then applied.

The polymeric film is applied to the core, for example, by wrapping it round the core. Alternatively, polymeric films are placed in the two hollow parts of a two-shell mould inside of which is placed the core.

Sterilisation of the implants obtained according to the invention is carried out by irradiation with gamma rays.

According to a preferred embodiment of the process of the invention, each of the polymeric films is applied successively to the core.

According to another embodiment of the process according to the invention, a polymeric film is applied to one part of the core, and a second polymeric film is applied to the remaining part of the core.

The core is advantageously composed of a biodegradable polymer, said polymer containing at least one active principle.

The polymeric film(s) of the sheath may also be composed of biodegradable polymers.

The biodegradable polymers of the core and/or of the polymeric film of the sheath may be chosen from the group comprising polycapiolactones, polyorthoesters and α-hydroxycarboxylic acids, preferably homopolymers and copolymers of lactic acid, glycolic acid and succinic acid.

Preferably, the polymeric film of the sheath is composed of a mixture, in proportions in the range 40:60 to 60:40, preferably 50:50, of a poly(lactic-co-glycolide) acid having a molecular weight which is in the range 20000 daltons to 100000 daltons, preferably in the range 40000 daltons to 60000 daltons and even more preferably 55,000 daltons, and a polylactide acid having a molecular weight preferably in the range 2000 daltons to 6000 daltons, and even more preferably 5000 daltons.

According to a preferred embodiment, the active principle used in the process according to the invention is an analogue of somatostatin or of one of the pharmaceutically acceptable salts thereof, preferably vapreotide pamoate.

Example 1

Production of an Implant According to the Invention

The process for the production of implants according to the invention comprises the following five stages:

1) Production of the core
2) Production of the coating film
3) Moulding the polymeric coating films
4) Placing the sheath around the core
5) Sterilisation.

1) Production of the core 3 g of an L-lactic acid polymer (known as L104 and sold by Boehringer Ingelheim, Ingelheim am Rhein, Germany) with a molecular weight of about 5000 daltons are mixed with 857 mg of the active principle known as RC 160 which is a vapreotide pamoate, a somatostatin analogue sold by Nova Biochem, Switzerland, using a three-dimensional mixer.

The mixture is homogenised in an agate mortar and then deionised.

The mixture obtained is extruded at a temperature of about 80° C. using a piston-type extruder with a die diameter of 1.5 mm.

The extrudate thus obtained is cut into rods 15 mm long.

2) Production of the coating film 1 g of the polymer RG 504 (sold by Boehringer Ingelheim) which is a poly(lactide-co-glycolide) polymer having a molecular weight of 55000 daltons and 1 g of the polymer L104 (L-PLA) (sold by Boehringer Ingelheim) having a molecular weight of 5000 daltons are mixed in a 50:50 mixture.

The mixture is then mixed on cylinders revolving one over the other, heated to 80° C. in order to homogenise the mixture.

The mixture is placed for 30 seconds between two non-stick sheets in a hydraulic press at a temperature of 75° C. whilst applying a pressure of 30 bars.

The film thus obtained is transparent and homogeneous and has a thickness of about 200 µm.

3) Moulding the polymeric coating films

The film obtained is cut into two parts. Each part is applied to the concave "female" part of a Teflon®-coated mould at a temperature of 65° C. A stamp forming the convex "male" part of said mould is placed on the film. The whole assembly is placed under a press at 65° C. for 30 seconds, this being the time taken to soften the film and form it in the mould.

The thickness of the sheath obtained is a function of the space between the two parts of the mould.

4) Placing the sheath around the core

The two polymeric films are left in their respective moulds. A cylindrical core with a length of 15 mm and a diameter of 1.5 mm is placed on one of them. The other polymeric film kept in its mould is placed on top. The whole assembly is placed under a press at 65° C. Nor one minute. The product is removed from the mould when the inside of the mould reaches a temperature of 50° C., thereby obtaining an implant according to the invention.

5) Sterilisation of the implant

The implant thus obtained is then sterilised by irradiation at 25 kGy at a temperature of −78° C. with γrays (source $^{60}$Co) at a rate of about 0.797 kGy/h.

6) In-vivo study of the effects of the implants

Implants obtained according to the method indicated above were place subcutaneously on the backs of Sprague-Dawley rats having an average weight in the range 330 g to 340 g.

Blood samples were taken after periods ranging from 24 hours to 260 days and the concentrations of active principle were determined by radio-immuno tests using a double antibody.

The results are set out in FIGS. 1 and 2.

What is claimed is:

1. An implant for the controlled release of at least one pharmaceutically active principle comprising:
    a core containing at least one active principle,
    and a sheath surrounding said core, wherein said sheath is composed of at least one polymeric film of controlled thickness, prepared before application, and applied around the core;
        wherein the polymeric film of the sheath is composed of a mixture, in proportions in the range 40:60 to 60:40, of a poly(lactide-co-glycolide) acid having a molecular weight which is in the range 20,000 daltons to 100,000 daltons, and a polylactide acid polymer, which is a polyester derived from an α-hydroxycarboxylic acid, having a molecular weight in the range 2,000 daltons to 6,000 daltons.

2. The implant for the controlled release of at least one pharmaceutically active principle according to claim 1, wherein the polymeric film of the sheath is composed of a mixture, in proportions 50:50, of a poly(lactide-co-glycolide) acid having a molecular weight which is in the range 20,000 daltons to 100,000 daltons, and a polylactide acid polymer, which is a polyester derived from an α-hydroxycarboxylic acid, having a molecular weight in the range 2,000 daltons to 6,000 daltons.

3. The implant for the controlled release of at least one pharmaceutically active principle according to claim 1, wherein the polymeric film of the sheath is composed of a mixture, in proportions in the range 40:60 to 60:40, of a poly(lactide-co-glycolide) acid having a molecular weight which is in the range 40,000 daltons to 60,000 daltons, and a polylactide acid polymer, which is a polyester derived from an α-hydroxycarboxylic acid, having a molecular weight of 5,000 daltons.

4. The implant for the controlled release of at least one pharmaceutically active principle according to claim 3, wherein the poly(lactide-co-glycolide) acid has a molecular weight of 55,000 daltons.

5. The implant for the controlled release of at least one pharmaceutically active principle according to claim 1, wherein the core is composed of a biodegradable polymer containing at least one active principle.

6. The implant for the controlled release of at least one pharmaceutically active principle according to claim 1, wherein at least one polymeric film forming the sheath contains at least one active principle.

7. The implant for the controlled release of at least one pharmaceutically active principle according to claim 1, wherein the active principle is an analogue of somatostatin or of one of the pharmaceutically acceptable salts thereof.

8. The implant for the controlled release of at least one pharmaceutically active principle according to claim 7, wherein the active principle is vapreotide pamoate.

9. A process for the preparation of an implant for the controlled release of at least one pharmaceutically active principle, wherein:
    a core containing at least one active principle is produced,
    at least one polymeric film of controlled thickness is prepared before application to the core,
    the polymeric film(s) is/are applied around said core by juxtaposing and superposing it/them,
    the implant thus obtained is sterilized,
        wherein the polymeric film of the sheath is composed of a mixture, in proportions in the range 40:60 to 60:40, of a poly(lactide-co-glycolide) acid having a molecular weight which is in the range 20,000 daltons to 100,000 daltons, and a polylactide acid polymer, which is a polyester derived from an α-hydroxycarboxylic acid, having a molecular weight in the range 2,000 daltons to 6,000 daltons.

10. A process for the preparation of an implant for the controlled release of at least one pharmaceutically active principle, wherein:
    a core containing at least one active principle is produced,
    at least one polymeric film of controlled thickness is prepared before application to the core,
    the polymeric film(s) is/are applied around said core by juxtaposing it/them,
    the implant thus obtained is sterilized,
        wherein the polymeric film of the sheath is composed of a mixture, in proportions in the range 40:60 to 60:40, of a poly(lactide-co-glycolide) acid having a molecular weight which is in the range 20,000 daltons to 100,000 daltons, and a polylactide acid polymer, which is a polyester derived from an α-hydroxycarboxylic acid, having a molecular weight in the range 2,000 daltons to 6,000 daltons.

11. A process for the preparation of an implant for the controlled release of at least one pharmaceutically active principle, wherein:
    a core containing at least one active principle is produced,
    at least one polymeric film of controlled thickness is prepared before application to the core,
    the polymeric film(s) is/are applied around said core by superposing it/them,
    the implant thus obtained is sterilized,
        wherein the polymeric film of the sheath is composed of a mixture, in proportions in the range 40:60 to 60:40, of a poly(lactide-co-glycolide) acid having a molecular weight which is in the range 20,000 daltons to 100,000 daltons, and a polylactide acid polymer, which is a polyester derived from an α-hydroxycarboxylic acid, having a molecular weight in the range 2,000 daltons to 6,000 daltons.

* * * * *